United States Patent
Ducreux et al.

(10) Patent No.: US 6,509,382 B1
(45) Date of Patent: Jan. 21, 2003

(54) PROCESS FOR ACTIVATING A FISCHER-TROPSCH SYNTHESIS CATALYST

(75) Inventors: Olivier Ducreux, Bougival (FR); Marie Claire Marion, Vernaison (FR); Magalie Roy-Auberger, Rueil Malmaison (FR); John Lynch, Rueil Malmaison (FR)

(73) Assignees: Institut Français du Petrole, Cédex (FR); AGIP Petroli S.p.A., Rome (IT); ENI S.p.A., Rome (IT)

( * ) Notice: Subject to any disclaimer, the term of this patent is extended or adjusted under 35 U.S.C. 154(b) by 0 days.

(21) Appl. No.: 09/717,101

(22) Filed: Nov. 22, 2000

(30) Foreign Application Priority Data

Nov. 22, 1999 (FR) ............................................. 99 14762

(51) Int. Cl.$^7$ ............................................. C07C 27/00
(52) U.S. Cl. ..................... 518/709; 518/700; 518/715
(58) Field of Search ................................. 518/700, 709, 518/715

(56) References Cited

U.S. PATENT DOCUMENTS 5,728,918 A * 3/1998 Nay et al. ................... 585/733

FOREIGN PATENT DOCUMENTS

| WO | WO 93/00993 | 1/1993 |
| WO | WO 97/17137 | 5/1997 |

OTHER PUBLICATIONS

Bukur et al., Activation studies with percipitated iron catalyst for F–T synthesis, J. Cata. (1995), 155 (2), 336–375.*

* cited by examiner

*Primary Examiner*—J. Parsa
(74) *Attorney, Agent, or Firm*—Millen, White, Zelano & Branigan, P.C.

(57) ABSTRACT

Process for activating a Fischer-Tropsch synthesis catalyst that comprises at least two stages:

at least one stage for activation in the presence of hydrogen, or a mixture of hydrogen and an inert gas, and at least one stage for activation in the presence of carbon monoxide or a mixture of carbon monoxide and an inert gas, and optionally a third activation stage that is carried out either in the presence of hydrogen or a mixture of hydrogen and an inert gas, or in the presence of carbon monoxide or a mixture of carbon monoxide and an inert gas.

13 Claims, No Drawings

PROCESS FOR ACTIVATING A FISCHER-TROPSCH SYNTHESIS CATALYST

This invention relates to a process for activating a catalyst that is used in a hydrocarbon synthesis process starting from a mixture that comprises CO—$H_3$—(CO2), i.e., a mixture that comprises carbon monoxide and hydrogen and that optionally comprises carbon dioxide, called synthesis gas.

Such a synthesis generally makes it possible to obtain a mixture of saturated linear hydrocarbons, preferably essentially consisting of C5+ hydrocarbons (i.e., that have at least 5 carbon atoms per molecule).

PRIOR ART

It is known to one skilled in the art that the synthesis gas can be converted into hydrocarbons in the presence of catalysts that contain transition metals, preferably cobalt or iron. This conversion is known in the literature under the name of Fischer-Tropsch synthesis.

Many methods have been used in the past either for activating the new catalyst or for regenerating it after use. In most of the cases, this activation treatment, also called reduction, is carried out on the new oxidized catalyst and consists of a temperature treatment of the catalyst in the presence of pure hydrogen or in the presence of a gas that contains hydrogen.

Patents EP-A-0 168 894 and EP-A-0 152 652 thus show the possibility of improving the performance levels of the catalysts by using various partial pressure conditions of hydrogen and flow rates, conditions that can be variable during the entire reduction stage.

U.S. Pat. No. 5,168,091 describes the possibility of reducing the catalyst under hydrogen by keeping a partial pressure of water below 0.1 MPa.

Patents EP-A-0 533 227 and EP-A-0 533 228 describe a method for reduction under hydrogen that makes it possible to optimize the activity of the catalysts by adjusting the pressures, on the one hand, and the flow rates, on the other hand.

Patents WO 97/17137 and U.S. Pat. No. 5,389,690 describe the advantages of a slurry phase reduction, i.e., with a catalyst in suspension in a liquid phase that consists of hydrocarbons. The catalyst is reduced in a single stage, at a partial pressure of hydrogen that is greater than 1.5 MPa.

Finally, Patent WO 93/00993 describes the advantages of an activation in a single stage, in the presence of a gas that contains carbon monoxide and less than 30% of hydrogen, preferably in the presence of carbon monoxide alone. Before activation, the catalyst comes in oxidized form. The catalyst that is thus obtained has an improved activity and an improved C5+ selectivity.

SUMMARY OF THE INVENTION

This invention relates to a process for activating a catalyst that makes it possible to carry out the hydrocarbon synthesis starting from a mixture that comprises carbon monoxide, hydrogen and optionally carbon dioxide (Fischer-Tropsch synthesis). Such a synthesis generally makes it possible to obtain a saturated linear hydrocarbon mixture.

The activation process according to the invention comprises at least two stages:

at least one stage for activation in the presence of hydrogen, or a mixture of hydrogen and an inert gas, and at least one stage for activation in the presence of carbon monoxide or a mixture of carbon monoxide and an inert gas, and optionally a third activation stage that is carried out either in the presence of hydrogen or a mixture of hydrogen and an inert gas, or in the presence of carbon monoxide or a mixture of carbon monoxide and an inert gas.

DETAILED DESCRIPTION OF THE INVENTION

This invention relates to a process for activating an active hydrocarbon synthesis catalyst starting from a mixture that comprises carbon monoxide and hydrogen, and optionally carbon dioxide. This synthesis is also called Fischer-Tropsch synthesis.

The activation process according to the invention comprises at least two stages:

at least one activation stage in the presence of hydrogen, or a mixture of hydrogen and inert gas, and at least one activation stage in the presence of carbon monoxide or a mixture of carbon monoxide and an inert gas.

The order of these stages is unimportant, but preferably during the activation with the process according to the invention, the catalyst is not brought into contact simultaneously with hydrogen and carbon monoxide.

One of the preferred embodiments of the activation process according to the invention is described below.

According to this first preferred method, the first stage (stage 1) is carried out in the presence of hydrogen or in the presence of a mixture of hydrogen and inert gas, at a temperature of between about 10° C. and about 700° C., preferably between about 100° C. and about 600° C. and more preferably between 200° C. and 500° C., at a pressure of between about 0.05 MPa and about 30 MPa, preferably between about 0.1 and about 10 MPa, more preferably between 0.1 and 2 MPa, at an hourly volumetric flow rate of between about 20 and about 100,000 $h^{-1}$ (volume of mixture per volume of catalyst and per hour), preferably between about 100 and about 40,000 $h^{-1}$. The duration of the first stage is generally greater than 10 minutes, preferably between 1 and 24 hours, according to the selected conditions of flow rate and temperature.

According to this first preferred method, the second stage (stage 2) is carried out in the presence of carbon monoxide or in the presence of a mixture of carbon monoxide and an inert gas, at a temperature of between about 10° C. and about 700° C., preferably between about 100° C. and about 600° C., and more preferably between 180° C. and 400° C., at a pressure of between about 0.05 MPa and about 30 MPa, preferably between about 0.1 and about 10 MPa, more preferably between 0.1 and 2 MPa, at an hourly volumetric flow rate of between about 20 and about 100,000 $h^{-1}$ (volume of mixture per volume of catalyst and per hour), preferably between about 50 and about 40,000 $h^{-1}$. The duration of the first stage is generally greater than 10 minutes, preferably between 1 and 24 hours, according to the flow rate and temperature conditions.

Another preferred embodiment of the activation process according to the invention consists in carrying out a first stage in the presence of carbon monoxide or a mixture of carbon monoxide and an inert gas, and a second stage in the presence of hydrogen or a mixture of hydrogen and an inert gas.

The two stages of this second preferred method are carried out under the conditions that are described above.

The first stage of this second preferred method is therefore carried out in the presence of carbon monoxide or a mixture of carbon monoxide and an inert gas, under the same conditions as stage 2 of the first preferred method. Likewise, the second stage in the presence of hydrogen or a mixture of hydrogen and an inert gas of this second preferred method is carried out under the same conditions as stage 1 of the first preferred method.

It is optionally possible to add a third stage to the activation process according to the invention. This third stage (stage 3) is also carried out either in the presence of hydrogen or a mixture of hydrogen and an inert gas, or in the presence of a carbon monoxide or a mixture of carbon monoxide and an inert gas, under conditions of temperature, pressure and flow rate that are identical to those that are indicated above for stages 1 or 2.

It is generally preferred to carry out at the end of each stage a purging under an inert gas to eliminate the traces of hydrogen or residual carbon monoxide.

All or part of these stages can be carried out in a gaseous phase or in a liquid phase. In the latter case, the catalyst is suspended in an inert solvent, for example a paraffinic fraction that preferably comprises at least one hydrocarbon that has at least 5, more preferably at least 10 carbon atoms per molecule, in particular and preferably in the case where a reaction for synthesis of hydrocarbons is used just after the activation stages and when this reaction is carried out in the presence of a liquid phase that preferably comprises at least one hydrocarbon that has at least 5, more preferably at least 10 carbon atoms per molecule.

The conversion of the synthesis gas into hydrocarbons generally takes place after the activation process and is generally operated under a total pressure that is usually between about 0.1 and about 15 MPa and preferably between about 1 and about 10 MPa, whereby the temperature is generally between about 150 and about 350° C. and preferably between about 170 and about 300° C.

The hourly volumetric flow rate is usually between about 50 and about 50,000 h$^{-1}$, preferably between about 100 and about 20,000 h$^{-1}$, and more preferably between 100 and 50,000 h$^{-1}$, and the molar ratio H2:CO in the synthesis gas is usually between about 1:2 and about 5:1, preferably between about 1.2:1 and about 2.5:1.

The activation process according to the invention that is described above can be used to activate a new catalyst in the oxidized state or to regenerate a used catalyst in the oxidized state or at least partly in the reduced state.

The catalyst is generally used either in the form of a calibrated fine powder that has a grain size of generally between about 10 and about 700 microns, or in the form of particles with an equivalent diameter that is generally between about 2 and about 10 mm. It is preferably used in the form of a calibrated fine powder when the activation process according to the invention is used in a liquid phase, and preferably in the form of particles when the activation process is used in a gaseous phase.

The catalyst generally comprises at least one metal of group VIII and a substrate. The element of group VIII of the periodic table is selected from among iron, cobalt and ruthenium. The metal of group VIII is preferably cobalt.

The substrate of the catalyst that can be used in the activation process according to the invention comprises at least one refractory oxide that is generally selected from among the oxides of magnesium, aluminum, silicon, titanium or zirconium, taken by themselves, mixed with one another or with oxides of other elements of the periodic table. The substrate that is used preferably will be selected from the group that consists of: alumina, silica, titanium oxide, carbon, aluminosilicates, and clays. Any other compound that can be used as a substrate can also be used, however. The substrate can be used in powder form or after shaping; any shaping technique that is known to one skilled in the art can be considered.

The catalyst that is used in the activation process according to the invention is preferably prepared by impregnation of at least one metal on a preformed substrate. A technique for preparing the catalyst is the impregnation of a solution that contains metal oxide particles and/or metal particles to be placed in suspension. The solvent can be an aqueous solvent, for example water, or an organic solvent.

The metal content of group VIII, expressed by weight of metal relative to the total weight of the catalyst, is generally between 0.1 and 50% by weight, preferably between 1 and 40% by weight, and more preferably between 5 and 30% by weight.

The catalyst can also contain other additional elements such as, for example, at least one alkaline metal, promoters such as, for example, at least one element that is selected from the group that consists of ruthenium, copper, molybdenum, tungsten, tantalum, titanium and scandium.

The content by weight of an additional element relative to the total weight of the catalyst is generally between 0.01 and 10% by weight, preferably between 0.1 and 5% by weight. These additional elements can be introduced at the same time as the metal of group VIII or in at least one subsequent stage.

In short, the process according to the invention is a process for activating a Fischer-Tropsch synthesis catalyst that comprises at least two stages:
  at least one stage for activation in the presence of hydrogen, or a mixture of hydrogen and an inert gas, and
  at least one stage for activation in the presence of carbon monoxide or a mixture of carbon monoxide and an inert gas.

In a first preferred embodiment, it can be a process for activating a Fischer-Tropsch synthesis catalyst that comprises at least two stages and in which:
  the first stage (stage 1) is carried out in the presence of hydrogen or a mixture of hydrogen and an inert gas,
  the second stage (stage 2) is carried out in the presence of carbon monoxide or a mixture of carbon monoxide and an inert gas.

In a second preferred embodiment, it can be a process for activating a Fischer-Tropsch synthesis catalyst that comprises at least two stages and in which:
  the first stage (stage 1) is carried out in the presence of carbon monoxide or a mixture of carbon monoxide and an inert gas,
  the second stage (stage 2) is carried out in the presence of hydrogen or a mixture of hydrogen and inert gas.

Stages 1 and 2 are preferably carried out at a temperature of between about 10° C. and about 700° C., at a pressure of between about 0.05 MPa and about 30 MPa, at an hourly volumetric flow rate of between about 20 and about 100,000 h$^{-1}$.

The activation process according to the invention can also comprise a third activation stage in the presence of hydrogen or a mixture of hydrogen and an inert gas. It can also optionally comprise a third activation stage in the presence of carbon monoxide or a mixture of carbon monoxide and an inert gas.

In a preferred way, a purging by an inert gas is carried out at the end of each stage of the process according to the invention.

According to one of the embodiments of the process according to the invention, a portion, and even all, of the stages can be carried out in gaseous phase. According to another embodiment of the process according to the invention, a portion and even all of the stages can be carried out in liquid phase. In the latter case, the liquid phase is preferably a paraffinic fraction. More preferably, said liquid phase comprises hydrocarbons that have at least 5 carbon atoms per molecule and more preferably at least 10 carbon atoms per molecule.

The process according to the invention makes it possible to activate any Fischer-Tropsch synthesis catalyst. It is particularly well suited, for example, for activating a catalyst that comprises at least one metal of group VIII and a substrate.

The following examples illustrate the invention.

EXAMPLE 1
(According to the Invention): Catalyst A

A catalyst of formulation $Co/Al2O3$ is prepared by impregnation of a cobalt nitrate solution in an alumina powder that has a specific surface area of 180 $m^2/g$. After impregnation, the substrate is dried at 120° C. and then calcined at 400° C. The cobalt content of the calcined catalyst is 12.5% by weight.

After calcination, 20 $cm^3$ of catalyst is reduced under pure hydrogen with a flow rate of 20 liters/hour (20 l/h) and at a temperature of 500° C., at atmospheric pressure and for 5 hours. Purging under nitrogen (20 l/h) is then carried out to eliminate all of the hydrogen, and the temperature is concomitantly decreased to 230° C.

When the temperature reaches 230° C., the catalyst is placed under a stream of pure carbon monoxide (10 l/h), still at atmospheric pressure and for 5 hours. Nitrogen purging is again carried out (flow rate 20 l/h), then a circulation of hydrogen (20 l/h) at atmospheric pressure and for 1 hour.

EXAMPLE 2
(For Comparison): Catalyst B

The same calcined solid as in Example 1 (20 $cm^3$) is reduced under pure hydrogen (flow rate 20 l/h) at a temperature of 500° C., at atmospheric pressure and for 5 hours.

EXAMPLE 3
(For Comparison): Catalyst C

A solid C is prepared according to the same method as in Example 1.

After calcination, the catalyst (20 $cm^3$) is reduced under a mixture of hydrogen and nitrogen (20% by volume of hydrogen—80% by volume of nitrogen, flow rate 40 l/h) at a temperature of 400° C., at atmospheric pressure and for 10 hours.

EXAMPLE 4
(According to the Invention): Catalyst D

A catalyst of formulation $CoRu/SiO_2$ is prepared from a silica substrate. The cobalt is impregnated in a first stage starting from a cobalt nitrate solution. The solid is then dried at 120° C. and calcined at 400° C.

The ruthenium is then impregnated in aqueous solution. The solid is dried at 110° C. and calcined at 300° C. The cobalt content is 15% by weight, and the ruthenium content is 0.25% by weight.

20 $cm^3$ of catalyst is then reduced under pure hydrogen (flow rate 20 l/h) at a temperature of 400° C. for 5 hours. Purging under nitrogen (flow rate 20 l/h) is then carried out to eliminate all of the hydrogen, and the temperature is concomitantly decreased to 220° C.

When the temperature reaches 220° C., the catalyst is placed under a stream of pure carbon monoxide (10 l/h), at atmospheric pressure and for 5 hours. Purging with nitrogen (flow rate 20 l/h) is then carried out again.

EXAMPLE 5
(For Comparison): Catalyst E

Catalyst E is prepared with the preparation method that is described in Example 4. After the calcination stage at 300° C. following the deposition of ruthenium, an activation treatment is undertaken on 20 $cm^3$ of catalyst E. This treatment comprises a single stage of reduction under pure hydrogen (flow rate 20 l/h) at a temperature of 400° C., at atmospheric pressure and for 5 hours.

EXAMPLE 6
(For Comparison): Catalyst F

A catalyst F (30 $cm^3$) is prepared from the same substrate with a silica base as in Example 4. In a first stage, the cobalt is impregnated starting from a cobalt nitrate solution. The solid is then dried at 120° C., calcined at 400° C., then reduced in a tubular reactor under pure hydrogen (30 l/h) at 400° C. and passivated under oxygen.

The ruthenium is then impregnated in aqueous solution. The solid is dried at 110° C., calcined at 300° C. and again reduced in a tubular reactor under pure hydrogen (30 l/h) at 400° C. and passivated under oxygen. The cobalt content is 15% by weight and the ruthenium content is 0.25% by weight.

20 $cm^3$ of catalyst F that is thus prepared is reduced under pure hydrogen at a flow rate of 20 l/h, at a temperature of 300° C., and at atmospheric pressure for 5 hours.

EXAMPLE 7
Catalytic Tests

Catalysts A, B, C, D, E, and F whose preparations are described in Examples 1 to 5 above are tested in a gaseous phase fixed bed in a unit that operates continuously and that operates on 20 $cm^3$ of catalyst after the reduction stage that is described in each of the examples corresponding to 1 to 6.

After the gaseous atmosphere is eliminated by means of purging under nitrogen, the catalysts are placed under test conditions of Fischer-Tropsch synthesis. These test conditions are as follows:

Temperature: 210 or 220° C.,

Pressure: 2 MPa

Hourly volumetric flow rate (VVH): 1500 $h^{-1}$ (volume of gas per volume of catalyst and per hour)

Molar ratio $H_2:CO=2:1$

TABLE

Conversion of Synthesis Gas into Hydrocarbons

| Catalyst | Temp. (° C.) | CO Conversion (% by volume) | Distribution of the Products that are Formed (% by weight) | |
| --- | --- | --- | --- | --- |
| | | | $C_1$ | $C_5+$ |
| A (invention) | 210 | 56 | 10 | 75 |
| B (for comparison) | 210 | 35 | 20 | 55 |
| C (for comparison) | 210 | 50 | 15 | 60 |
| D (invention) | 220 | 75 | 12 | 65 |

TABLE-continued

Conversion of Synthesis Gas into Hydrocarbons

| Catalyst | Temp. (° C.) | CO Conversion (% by volume) | Distribution of the Products that are Formed (% by weight) | |
| --- | --- | --- | --- | --- |
| | | | $C_1$ | $C_5+$ |
| E (For comparison) | 220 | 66 | 18 | 52 |
| F (For comparison) | 220 | 65 | 25 | 49 |

The results of the table show that the activation process according to the invention leads to an improved output of heavy products relative to the activation processes of the prior art.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 99/14.762 are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for activating a Fischer-Tropsch synthesis catalyst that comprises at least two stages:
   at least one stage for activation in the presence of hydrogen, or a mixture of hydrogen and an inert gas, and
   at least one stage for activation in the presence of carbon monoxide or a mixture of carbon monoxide and an inert gas.

2. A process according to claim 1 for activating a Fischer-Tropsch synthesis catalyst that comprises at least two stages and in which:
   a first stage is carried out in the presence of hydrogen or a mixture of hydrogen and an insert gas, and after conducting the first stage,
   a second stage is carried out in the presence of carbon monoxide or a mixture of carbon monoxide and an inert gas.

3. A process according to claim 1 for activating a Fischer-Tropsch synthesis catalyst that comprises at least two stages and in which:
   a first stage is carried out in the presence of carbon monoxide or a mixture of carbon monoxide and inert gas, and after conducting the first stage,
   a second stage is carried out in the presence of hydrogen or a mixture of hydrogen and inert gas.

4. A process according to claim 1, in which the stages are carried out at a temperature of between about 10° C. and about 700° C., at a pressure of between about 0.05 MPa and about 30 MPa, at an hourly volumetric flow rate of between about 20 and about 100,000 $h^{-1}$.

5. A process according to claim 2 that also comprises a third activation stage in the presence of hydrogen or a mixture of hydrogen and an inert gas.

6. A process according to claim 3 that also comprises a third activation stage in the presence of carbon monoxide or a mixture of carbon monoxide and an inert gas.

7. A process according to claim 1, in which the catalyst is not brought into contact simultaneously with hydrogen and carbon monoxide.

8. A process according to claim 1, in which purging by an inert gas is carried out at the end of each stage.

9. A process according to claim 1, in which all of the stages are carried out in a gaseous phase.

10. A process according to claim 1, in which all of the stages are carried out in liquid phase.

11. A process according to claim 10, in which the liquid phase is a paraffinic fraction that comprises hydrocarbons that have at least 5 carbon atoms per molecule.

12. A process according to claim 1, in which the catalyst comprises at least one metal of group VIII and a substrate.

13. A process for activating a Fischer-Tropsch synthesis catalyst that comprises at least two stages:
   at least one stage for activation in the presence of hydrogen, or a mixture of hydrogen and an inert gas,
   at least one stage for activation in the presence of carbon monoxide or a mixture of carbon monoxide and an inert gas, and
   a third activation stage in the presence of carbon monoxide, hydrogen, a mixture of carbon monoxide and inert gas or a mixture of hydrogen and inert gas.

* * * * *